(12) United States Patent
O'Ruanaidh et al.

(10) Patent No.: US 8,109,878 B1
(45) Date of Patent: Feb. 7, 2012

(54) USE OF CODED EXCITATION SCHEMES IN THE DETECTION AND LOCATION OF A TARGET IN A HUMAN BODY SUCH AS BREAST CALCIFICATIONS

(75) Inventors: Joseph O'Ruanaidh, Hamilton, NJ (US); David Steven Graff, Reading, PA (US); Christopher J. Vecchio, Philadelphia, PA (US); Edmond Rambod, Los Angeles, CA (US); Robert M. Snukal, Santa Monica, CA (US)

(73) Assignee: Quantason, LLC, Philadelphia, PA (US)

( * ) Notice: Subject to any disclaimer, the term of this patent is extended or adjusted under 35 U.S.C. 154(b) by 0 days.

(21) Appl. No.: 12/807,845

(22) Filed: Sep. 14, 2010

(51) Int. Cl.
  *A61B 8/00* (2006.01)
  *A61B 8/14* (2006.01)
(52) U.S. Cl. ............. 600/443; 600/437; 73/584; 73/587
(58) Field of Classification Search .......... 600/436–437, 600/443, 447, 448; 324/179; 73/584, 589, 73/599, 620; 342/176, 190
See application file for complete search history.

(56) References Cited

U.S. PATENT DOCUMENTS

| | | | | |
|---|---|---|---|---|
| 6,130,641 A * | 10/2000 | Kraeutner et al. | ............ | 342/179 |
| 2003/0004413 A1 * | 1/2003 | Inoue et al. | ................... | 600/436 |
| 2009/0247869 A1 | 10/2009 | Rambod | | |

OTHER PUBLICATIONS

Bradford W. Parkinson, *The Global Positioning System*: theory and applications. 1996.
Smith, P., FURSE, C. *Feasibility of Spread Sensors for Location of Arcs on Live Wires*. IEEE Sensors, 5, 6 1445 (2005).
Burnsweig, J., Woodridge, J., *Ranging and Data Transmission Using Digital Encoded FM "Chirp" Surface Acoustic Wave Filters*, IEEE Transactions ond Sonics and Ultrasonics, 20, 2, 190 (1973).
*Experimental Verification of Real-Valued Orthogonal PN Sequence Applied to Pulse Compression Sonar*. Electronics and communications in Japan, Part I (communications), 75, 3, 72 (2007).
*Metal Fatigue in Old Aircraft. Flying Rivets. A New Technique that Listens for Cracks in Ageing Aircraft*. The Economist. (Aug. 5, 2010).
Thanassis, X. Misaridis et al., *Potential of Coded Excitation in Medical Ultrasound Imaging*. Ultrasonics, vol. 38 (2000), pp. 183-189.

* cited by examiner

*Primary Examiner* — Brian Casler
*Assistant Examiner* — Michael N Fisher
(74) *Attorney, Agent, or Firm* — Thomas I. Rozsa

(57) ABSTRACT

A method for detecting a target or targets in a medium. The method incorporates generating beams of ultrasonic wave energy each having a modulation envelope and causing each beam of wave energy to impact a target region having a multiplicity of targets and demodulating each signal generated by vibration of each target caused by the interaction of a respective ultrasound wave energy beam having a modulation envelope with each of the targets and receiving each demodulated signal from each target by a multiplicity of sensors. Thereafter, each time-of-flight of each demodulated signal from each of the targets to each of the multiplicity of sensors is computed to determine the location of a respective target.

32 Claims, 11 Drawing Sheets

USE OF CODED EXCITATION SCHEMES IN THE DETECTION AND LOCATION OF A TARGET IN A HUMAN BODY SUCH AS BREAST CALCIFICATIONS

BACKGROUND OF THE INVENTION

1. Field of the Invention

The present invention relates, in general, to the detection of targets within the human body. The present invention also relates in particular to the detection and localization of microcalcifications in the human breast which may be indicative of the presence of breast cancer.

2. Description of the Prior Art

Breast cancer is often characterized by the presence of calcifications along mammary ducts. These may be detected using X-ray mammography techniques. Unfortunately, mammograms have a number of drawbacks. First, calcifications appear as white/shiny dots in a generally black-and-white background. Fibroglandular tissue, which is normal in breasts, also appears as white which leads to poor contrast in mammographic images. Second, X-ray mammography is an extremely uncomfortable procedure. Third, mammography is an x-ray based modality which involves exposure to harmful ionizing radiation.

An alternative approach, which does lead to better quality images, is to use an MRI. However, MRI may be prohibitively expensive and out of reach for all but a limited number of patients with certain socioeconomic standing.

The concept of using conventional ultrasound imaging technologies to detect calcifications has, in general, been developed prior to this invention. The benefit of using ultrasound is that it is comfortable, affordable, portable, available in a broad number of locations and to a broad range of populations, is less-expensive than MRI and does not impose any harmful radiation such as X-rays. Moreover, in cases with dense breasts, mammograms have proven to have limited utility and therefore, ultrasound is the only method of choice, next to expensive and unaffordable MRI.

United States Published Patent Application 20090247869 describes an approach using ultrasound in conjunction with four or more receiving contact microphones or sensors located on a ring which is positioned on or around the human breast. These sensors are meant to detect sound radiation radiated from an emitting source or multiplicity of emitting sources. A signal emitted from a given location will arrive at each of the receiving sensors at a time determined by the distance between the source and the sensor. Since the speed of sound is constant and finite in different layers of the human breast, the signal will arrive at each of the receiving sensors at different times. If one can precisely estimate the time delays then, in theory, one can locate the position of the emitting source. According to this invention, an ultrasound imaging transducer is used to deliver certain acoustic force to and thereby stimulate a target or multiplicity of targets of acoustic radiation such as microcalcifications. The resulting sound signals, which have markedly different frequencies than the transmitted ultrasound frequencies (i.e., kilohertz response versus megahertz transmitted ultrasound frequencies) are then received by the receiving sensors. Data acquired by the sensors will allow one to determine the location of the microcalcifications in the breast assuming that the relative positions and configurations of the sensors and excitation transducer are known.

The following eight publications and standards are the closest prior art that are relevant to the field of the present invention:

1. United States Published Patent Application No. 20090247869, Rambod, Edmond, et al. Oct. 1, 2009, "Application of Image-based Dynamic Ultrasound Spectrography (IDUS) in detection and localization of breast micro-calcifications."
2. *The Global Positioning System: Theory and Applications*, Bradford W. Parkinson, James J. Spilker. 1996.
3. *Feasibility of Spread Spectrum Sensors for Location of Arcs on Live Wires*, IEEE Sensors, Vol. 5, No. 6, 1445 (2005),
4. *Ranging and Data Transmission Using Digital Encoded FM "Chirp" Surface Acoustic Wave Filters, IEEE Transactions on Sonics and Ultrasonics,* 20, 2, 190 (1973).
5. IEEE Standard 802.15.4a-2007.
6. *Experimental Verification of Real-Valued Orthogonal PN Sequence Applied to Pulse Compression Sonar, Electronics and Communications in Japan, Part I (communications)*, 75, 3, 72 (2007).
7. *Metal Fatigue in Old Aircraft. Flying Rivets. A New Technique that Listens for Cracks in Ageing Aircraft. The Economist.* (Aug. 5, 2010).
8. *Potential of Coded Excitation in Medical Ultrasound Imaging. Ultrasonics*, Vol. 38 (2000) pp. 183-189.

The prior art requires knowledge of the location of the receiving sensors in an array but provides no explicit method for determining the locations. The prior art describes the use of a sensor array to determine the location of a target or multiplicity of targets based upon the phase delays of signals received from the target or targets but does not describe the format in which the signals should be best generated, acquired, processed, or best interpreted. There has been extensive prior art using coded signals with sharp autocorrelation functions to determine distances in radar, sonar, wire-fault-detection, and direct ultrasound imaging, but there has been no application of coded signals to Image-based Dynamic Ultrasound Spectrography (IDUS), Acoustic Radiation Force Imaging (ARFI), or similar imaging modalities.

A rigid mechanical framework could be used to position the sensors and transducer in fixed, known locations relative to one another but this arrangement is less than ideal in terms of adaptability and the need to maintain contact with the body.

The prior art describes the use of time-of-flight measurements to determine the location of a source of acoustic radiation such as a calcification or other target excited by a modulated ultrasound signal but does not specify a format for the excitation/stimulation signal.

SUMMARY OF THE INVENTION

This invention relates to diagnostic and screening medical ultrasound in general and to ultrasound-stimulated detection and location of calcifications in a human body, Image-based Dynamic Ultrasound Spectrography (IDUS), Acoustic Radiation Force Imaging (ARFI), and similar imaging modalities in particular. It documents a means of exciting the characteristic frequencies of objects embedded in breast tissue and determining the positions and distributions of microcalcifications and tumors with respect to a receiving sensor or multiplicity of receiving sensors and a transmitting ultrasonic transducer.

In addition to facilitating the task of locating a sound source, this invention also provides a means to dynamically determine or verify the location of the associated sensors (if they are also capable of acting as sound sources) which permits the use of a flexible array matrix. A flexible array matrix facilitates adaptability to different physical situations and makes it easier to maintain acoustic coupling with the body.

This invention describes a transmission method in which a modulation envelope is applied to an ultrasound signal. In addition to facilitating the task of locating a sound source, the modulation envelopes described herein have advantages over other envelopes in terms of enhancing the ability to detect or receive the signals emanating from a sound source in the presence of noise or clutter signals.

While the prior art describes the use of time-of-flight measurements to determine the location of a source of acoustic radiation such as a calcification or other target excited by a modulated ultrasound signal, it does not specify a format for the excitation/stimulation signal. The present invention describes an advantageous means of designing excitation/stimulation signals for this application.

The IDUS medical imaging modality relies on an array of acoustic sensors placed around or adjacent to a human breast or other part of the body. The sensors can be arranged in the form of a ring, can be in any random arrangement of locations, or can be positioned in specifically chosen locations. The sensors can all be located in the same plane or in any 3-dimensional configuration. An ultrasonic imaging and excitation transducer generates certain stimulating signals which are received by the breast tissues and which, if they contact a microcalcification, other target, or any region with sharply different mechanical and visco-elastic properties, will result in reflected, demodulated, or re-radiated signals. These signals will propagate away from the microcalcification or other targets and can be detected by the various receiving sensors. In order to make the best use of the signals received by the sensors, the sensors' locations must be known with respect to one another and with respect to the excitation transducer, but these locations can be determined using the technologies described herein.

When used in this application, the term "sensor" applies to an acoustic sensor and "acoustic sensor" can include the following: a microphone, microphones, a hydrophone, hydrophones, an accelerometer, accelerometers, a strain gauge, strain gauges, a surface microphone, surface microphones, a surface hydrophone and surface hydrophones. It is understood that when the term "sensor" is set forth in this application, it includes all of the above.

In order to detect a target and to determine that a detected target is present in a medium such as a human breast, at least one sensor is required. In order to obtain the three dimensional location of the target such as a microcalcification in a medium such as a human breast, at least three sensors are required.

It is an object of the present invention to provide a method of detecting a target in a medium, comprising:
 a. generating an ultrasound signal having a modulation envelope and causing the ultrasound signal to impact a target;
 b. demodulating the ultrasound signal having a modulation envelope through the interaction of the ultrasound signal having a modulation envelope and the target and receiving the demodulated signal by at least one sensor to detect that a target is present in the medium.

Once it has been determined that a target is in the medium, the present invention provides a method for determining a location of a detected target in one dimension in the medium by computing a time-of-flight of the demodulated signal to the at least one sensor having a known location and determining the shortest time-of-flight to determine a direct path from the detected target to at least one sensor, the direct path corresponding to the distance between the detected target and the at least one sensor.

Once it has been determined that a target is in the medium, the present invention also provides a method for determining a location of a detected target in three dimensions in the medium by computing each time-of-flight of the demodulated signal to each of a multiplicity of at least three sensors having known locations and determining the shortest time-of-flight from at least three sensors to the detected target to determine each direct path from the detected target to each of the at least three sensors, each direct path corresponding to the distance between a respective one of the three sensors and the detected target in the medium.

The modulation envelope of the generated ultrasonic signal is designed to supply stimulation energy to the target over a broad range of frequencies.

The modulation envelope of the generated ultrasound signal is based on a sequence whose cyclic autocorrelation function approximates a delta function.

The modulation envelope of the generated ultrasound signal is selected from the group consisting of a chirp, based on a pseudorandom sequence, based on a maximum length sequence, based on a Gold sequence, and is intended to improve reception of the desired signal in the presence of multipath or clutter signals.

The ultrasound signals can be generated from one single element ultrasonic transducer (see FIG. 7) or from an ultrasonic array transducer (see FIG. 8). An ultrasonic array transducer has multiple transducer elements. An example of an ultrasonic array transducer is a typical medical imaging array probe.

The target can be a microcalcification or calcification in a human breast or a cluster of microcalcifications or calcifications in a human breast.

The medium is biological tissue which is a part of a human body, in particular a human breast.

The present invention method can also be used in conjunction with Image-based Dynamic Ultrasound Spectrography (IDUS).

The present invention method also comprises transmission of the demodulated signal generated by the interaction of the ultrasound signal having a modulation envelope and the target to the sensors which is selected from the group consisting of reflection, re-radiation and demodulation.

The generated ultrasound signal is obtained from an ultrasonic transducer selected from the group consisting of a single element transducer and an array transducer.

The sensors can include: an acoustic sensor or sensors, a microphone, microphones, a hydrophone, hydrophones, an accelerometer, accelerometers, a strain gauge, strain gauges, a surface microphone, surface microphones, a surface hydrophone and surface hydrophones.

It is a further object of the present invention to provide a method of detecting targets in a medium, comprising:
 a. generating beams of ultrasonic wave energy each having a modulation envelope and causing each beam of ultrasonic wave energy to impact a target region in the medium having a multiplicity of targets;
 b. demodulating the ultrasound wave energy beams having a modulation envelope through the interaction of the ultrasound wave energy beams having a modulation envelope and each of the targets and receiving each demodulated signal from each target by a multiplicity of sensors.

Once targets have been detected in the medium, it is also an object of the present invention to determine the location of the targets. The target locations can be determined by computing each time-of-flight of each demodulated signal from each of the targets to each of the multiplicity of sensors having known locations and determining the shortest time-of-flight from each target to each sensor to identify the direct path from each target to each of the multiplicity of sensors, each direct path corresponding to the distance between a respective target in the medium and a respective sensor.

The modulation envelope of the generated beams of ultrasonic wave energy is designed to supply stimulation energy to the target over a broad range of frequencies.

The modulation envelope of the generated beams of ultrasonic wave energy is based on a sequence whose cyclic autocorrelation function approximates a delta function.

The modulation envelope of the generated beams of ultrasonic wave energy is selected from the group consisting of a chirp, based on a pseudorandom sequence, based on a maximum length sequence, based on a Gold sequence, and is intended to improve reception of the desired signal in the presence of multipath or clutter signals.

The beams of ultrasound wave energy can be generated from one single element ultrasonic transducer or from an ultrasonic array transducer. An ultrasonic array transducer has multiple transducer elements. An example of an ultrasonic array transducer is a typical medical imaging array probe.

The target can be a microcalcification or calcification in a human breast or a cluster of adjacent microcalcifications or calcifications in a human breast.

The medium is biological tissue which is a part of a human body, in particular a human breast.

The sensors can include: an acoustic sensor or sensors, a microphone, microphones, a hydrophone, hydrophones, an accelerometer, accelerometers, a strain gauge, strain gauges, a surface microphone, surface microphones, a surface hydrophone and surface hydrophones.

The medium is biological tissue which is a part of a human body, in particular a human breast.

The present invention method can also be used in conjunction with Image-based Dynamic Ultrasound Spectrography (IDUS).

The present invention method also comprises transmission of the demodulated signal generated by the interaction of the ultrasound signal having a modulation envelope and the target to the sensors which is selected from the group consisting of reflection, re-radiation and demodulation.

The generated ultrasound signal is obtained from an ultrasonic transducer selected from the group consisting of a single element transducer and an array transducer It is an additional object of the present invention to provide a method for detecting at least one target in a medium, comprising:
  a. generating at least one beam of ultrasonic wave energy having a modulation envelope and causing the at least one beam of ultrasonic wave energy to impact a target region in the medium having at least one target;
  b. demodulating the at least one beam of ultrasonic wave energy having a modulation envelope through the interaction of the at least one beam of ultrasonic wave energy having a modulation envelope and the at least one target and receiving at least one demodulated signal from the at least one target by at least one sensor to determine that at least one detected target is present in the medium.

Once it has been determined that at least one target is in the medium, the present invention encompasses a method to determine a location of at least one detected target in one dimension in the medium by computing a time-of-flight of the at least one demodulated signal from the at least one detected target to at least one sensor having a known location and determining the shortest time-of-flight from the at least one detected target to the at least one sensor to determine the direct path from the at least one detected target to the at least one sensor, the direct path corresponding to the distance between the at least one detected target in the medium and the at least one sensor.

In addition, once it has been determined that a target is in the medium, the present invention also includes a method for determining a location of at least one detected target in three dimensions in the medium by computing each time-of-flight of the at least one demodulated signal to each of a multiplicity of at least three sensors having known locations and determining the shortest time-of-flight from the at least three sensors to the at least one detected target to determine each direct path from the at least one detected target to each of the at least three sensor, each respective direct path corresponding to the distance between a respective one of the three sensors and the at least one detected target.

The modulation envelope of the generated at least one beam of ultrasonic wave energy is designed to supply stimulation energy to the at least one target over a broad range of frequencies.

The modulation envelope of the generated at least one beam of ultrasonic wave energy is based on a sequence whose cyclic autocorrelation function approximates a delta function.

The modulation envelope of the generated at least one beam of ultrasonic wave energy is selected from the group consisting of a chirp, based on a pseudorandom sequence, based on a maximum length sequence, based on a Gold sequence, and is intended to improve reception of the desired signal in the presence of multipath or clutter signals.

The at least one beam of ultrasound wave energy can be generated from one single element ultrasonic transducer or from an ultrasonic array transducer. An ultrasonic array transducer has multiple transducer elements. An example of an ultrasonic array transducer is a typical medical imaging array probe.

The target can be a microcalcification in a human breast or a cluster of adjacent microcalcifications in a human breast.

The medium is biological tissue which is a part of a human body, in particular a human breast.

The sensors can include: an acoustic sensor or sensors, a microphone, microphones, a hydrophone, hydrophones, an accelerometer, accelerometers, a strain gauge, strain gauges, a surface microphone, surface microphones, a surface hydrophone and surface hydrophones.

The medium is biological tissue which is a part of a human body, in particular a human breast.

The present invention method can also be used in conjunction with Image-based Dynamic Ultrasound Spectrography (IDUS).

The present invention method also comprises transmission of the demodulated signal generated by the interaction of the ultrasound signal having a modulation envelope and the target to the sensors which is selected from the group consisting of reflection, re-radiation and demodulation.

The generated ultrasound signal is obtained from an ultrasonic transducer selected from the group consisting of a single element transducer and an array transducer.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Figure 1:
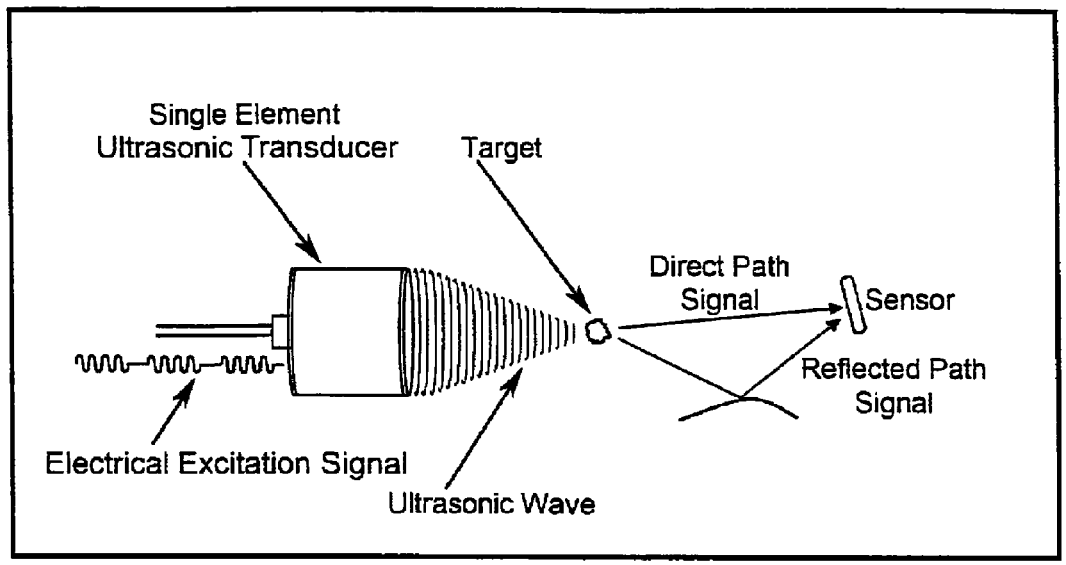
FIG. 1 is a diagram showing a single element transducer applying a modulated radiation force, or a modulated ultrasound signal, or a modulated beam of ultrasound wave energy to a target in a medium such as biological tissue and the resulting demodulated signal traveling by the direct path and by a reflected path from the target to a receiving acoustic sensor.
Figure 2A:
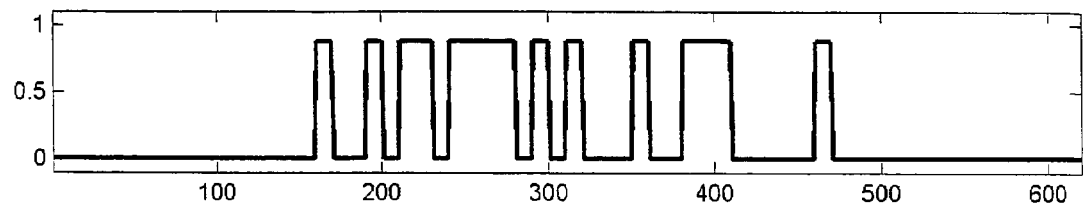
FIG. 2A is a waveform of a first signal delayed by a first amount of time as a result of traveling along a first path.
Figure 2B:
FIG. 2B is a waveform of a second signal delayed by a second amount of time as a result of traveling along a second path.
Figure 2C:
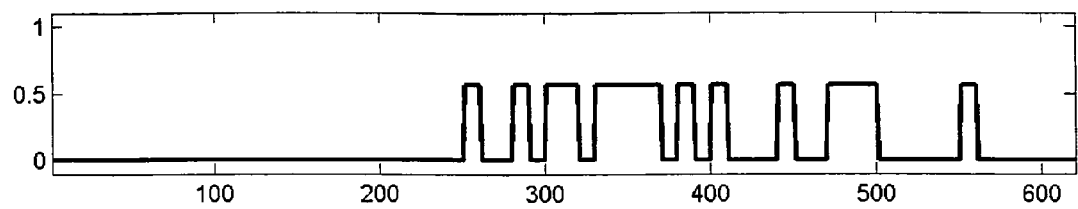
FIG. 2C is a waveform of a third signal delayed by a third amount of time as a result of traveling along a third path.
Figure 2D:
FIG. 2D is a waveform of a fourth signal delayed by a fourth amount of time as a result of traveling along a fourth path.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The nature of the sound transmission medium, in this case human breast tissues, can vary widely. In addition, physical features of interest such as microcalcifications and tumors may be characterized by rough edges, branching structures, irregular geometries, and complex spatial distributions, and thereby may respond to a stimulating signal or multiplicity of stimulating signals and emit signal energy or energies over a wide range of frequencies. For this reason it is advantageous to use a wideband stimulation signal or sequence of signals.

A standard method of generating a wideband stimulation sequence is to use a linear chirp. Like chirped signals, maximal length sequences have (except for a DC offset) flat spectral density and equivalently a delta function auto-correlation function. A narrow (in time) auto-correlation function of this sort with minimal sidelobes, has certain advantages when attempting to make time-of-flight or response delay measurements. Generating a chirped signal may be difficult, or even impossible, using certain hardware. There is a wide class of digital pseudo-noise sequences which also have a sharp auto-correlation function which would be particularly well suited to hardware and transducers which emit constant amplitude pulses. One example of this class are the maximal length sequences (herein referred to as "m-sequences") which are easy to implement in hardware using linear shift feedback registers. Other sequences include Gold codes, Kasami sequences and Walsh Hadarnard Transfom basis functions.

One approach to time-of-flight measurement would be to measure the impulse response of the transmission path, since the first peak of the impulse response occurs at a time equal to the delay time of the transmission channel. This may be accomplished by applying an m-sequence as a spreading code or "chipping sequence" to the input at the transducer. In any linear system, the Fourier Transform of the impulse response is the ratio of the Fourier Transform of the output signal divided by the Fourier Transform of the input signal. If the numerator and denominator are multiplied by the complex conjugate of the Fourier Transform of the input signal, the following result is desired. The impulse response of the transmission path (and hence the transmission delay) is then computed by determining the Fourier transform of the cross-correlation of the input m-sequence with the corresponding received signal (the output of the channel) and dividing this by the Fourier transform of autocorrelation of the input m-sequence. The transfer function H(f) of the transmission path is therefore defined by:

$$H(f) = \frac{G_{xy}(f)}{G_{xx}(f)}$$

where $G_{xx}$ is the auto spectrum of the m-sequence excitation or stimulation signal and $G_{xy}$ is the cross spectrum of the response with respect to the excitation. Once H(f) is known, then the impulse response function h(t) may be found by inverse Fourier transforming H(f). Note that m-sequences have the property that the power spectral density (which is the Fourier transform of the autocorrelation function) is "flat". In other words, the denominator Gxx(f) of H(f) is constant for all frequencies (except zero) and is normally ignored. Equivalently, on may described this approach as "correlating" the received output signal with the input m-sequence to obtain the impulse response or delay characteristics of the transmission path.

Figure 3:
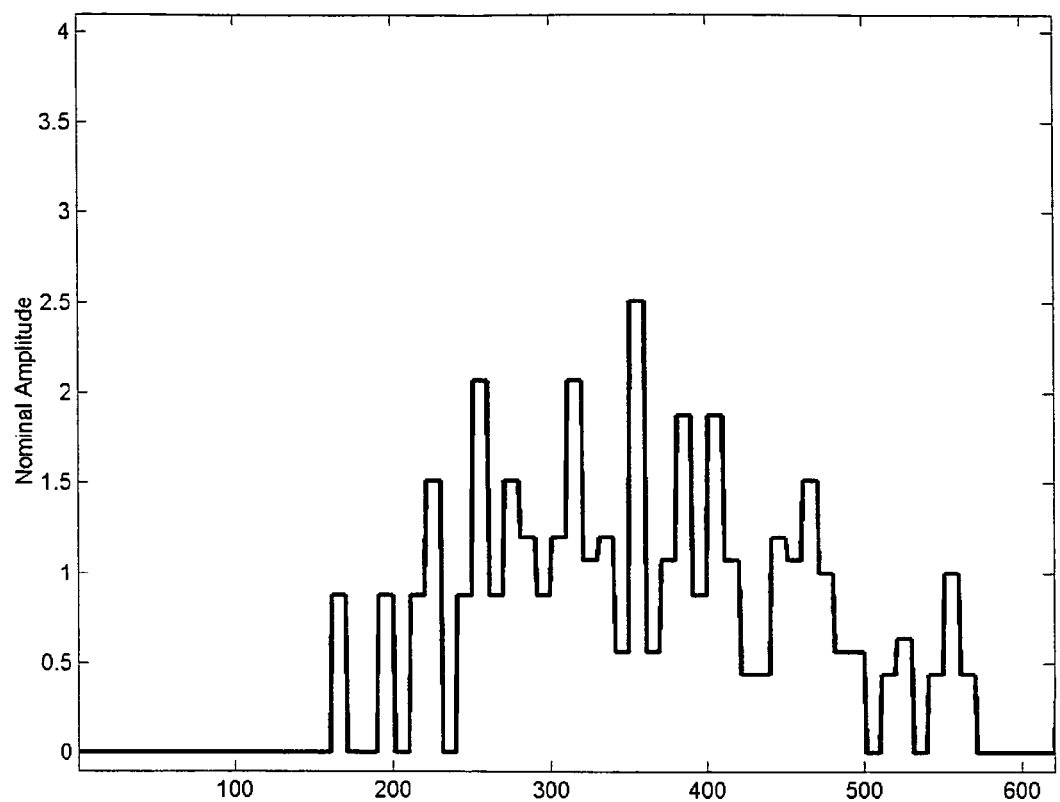
FIG. 3 is a waveform of the total received signal at a sensor as the sum of the signals arriving along each of the multiple paths illustrated in FIGS. 2A, 2B, 2C and 2D.
Figure 4:
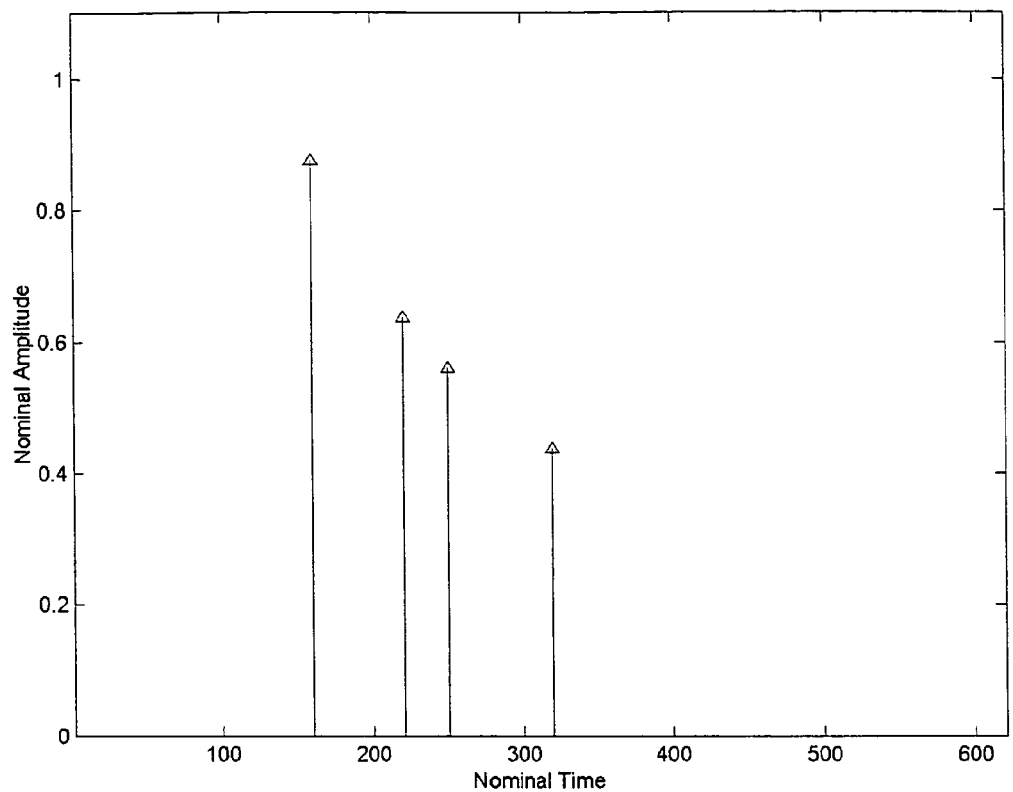
FIG. 4 illustrates the correlation of the total received signal with the known input m-sequence. This is the "impulse response" and it shows that a single transmitted impulse is received as four separate impulses arriving with different delays. The position of the leading impulse is of particular interest because it shows the delay of time along the direct path.

Acoustic or ultrasound signals can travel through biological tissue in all directions and can be reflected off of objects and interfaces. FIG. 1 shows a signal traveling by the direct path and by a reflected path from a target to a sensor. The signal is generated by an ultrasonic transducer applying a modulated radiation force to a target. FIGS. 2A, 2B, 2C, and 2D, 3 and 4 comprise a montage of three related graphs. For each graph, the X-axis is time and the Y-axis is amplitude. These axes are all in normal units. The first montage of FIGS. 2A, 2B, 2C and 2D shows a signal delayed by four different amounts as a result of traveling along four different paths. FIG. 3 shows the total received signal at a sensor as the sum of the signals arriving along each of the multiple paths. FIG. 4 shows the correlation of the total received signal with the known input m-sequence. This is the "impulse response" of the transmission channel. This shows that a single transmitted impulse is received as four separate impulses arriving with different delays. The position of the leading impulse is of particular interest because it shows the delay along the direct path and as described later, can be used to determine the position of the target.

The impulse response of the transmission path gives a relatively simple way of determining the total time-of-flight between the transmitting transducer to the target and, subsequently, from the target to the receiving sensor or multiplicity of sensors. The first significant peak in the impulse response of the transmission path (normally) corresponds to the direct (linear) path, though the system may have to be tuned or trained on data of known distances to compensate for other delays in the system and modifications of the signal.

One subtle point in apply m-sequences is the desirable autocorrelation properties of the m-sequence strictly apply only to cyclic shifts of the m-sequence. This can be implemented by correlating the output with repeated copies of the input of the m-sequence or by using Fourier techniques to compute the cross correlation. There is no ambiguity caused by this wrap-around since the delays scene in practice is always much smaller than the length of the m-sequence. For example, a distance of 0.15 m corresponds to a time delay of approximately 100 microseconds for sound propagating in water. At a sampling rate of 200 kHz, this corresponds to only 20 sample periods.

The delay determined by this system corresponds to the total distance from the ultrasound transducer to the target plus the distance from the target to a given receiver. Points of constant total distance lie on an ellipsoid with the transducer and a receiver located at the two foci. There is a separate ellipsoid for each receiver so, mathematically, locating the target is equivalent to finding the point of intersection between a set of ellipsoids. It is thus necessary to know the position of the receiver(s) with respect to the ultrasound transducer. In typical ultrasound transducers, there is a tight focal area, and only one component of the position of the target (the distance from the transducer) will need to be determined, so that, in principle, only a single path length will be needed to locate the target at the intersection of the ellipsoid with the focal axis of the transmitted signal.

In a realistic situation, the demodulated signal may be distorted by the target and may experience interference from other signals or reflections. These signals will typically appear displaced to positive delays in the auto-correlation function. However, they still may interfere with the interpretation of the distance from the target. In these situations a multiplicity of receiving sensors can be used to better determine the true direct path distance.

In one implementation, the receiving sensors are fixed in a solid container and have known locations with respect to the ultrasound transducer. In other implementations, the receiving sensors are affixed individually to the human breast at unknown locations. The method of choice to determine the location of the emitting target is to use numerical optimization to minimize a distance metric or "Cost Function" as defined by:

$$C(x) = \Sigma_{i=1}^{M} ||x|_2 + |x - p_i|_2 - c\Delta t_i|_2$$

where x is the vector position of the source, $p_i$ is the position of each of the M sensors, $\Delta t_i$ is the delay at each sensor, c is the speed of sound and the origin is the position of the transmitting transducer. The symbol $|x-p_i|_2$ denotes the 2-norm or Euclidean norm of the vector, namely the square root of the sum of the squares of the elements; for example $|(3, 4, 12)|_2$ equals 13. The vector x that minimizes the cost function yields the optimal estimate for the position of the source. Note that this method is resilient to errors because even if one or some of the receiving sensors display poor estimates of time delay, the other sensors will jointly still estimate the position of the emitting source. This property is important because individual sensors may be poorly coupled, be located at the node of a standing wave, or not receive a direct path signal. However, the minimum number of receiving sensors to satisfy the Cost Function terms depends on the number of unknowns so, for example, location of a source in three dimensions would require data from at least three distinct sensors.

If the sensors are designed so that they may also be operated as sound sources, each sensor can also be used to generate an m-sequence or chirp which can be detected by the other sensors and decoded in a similar manner to a demodulated ultrasound signal received from a target. The distances between each sensor, the stimulating transducer, and each of the others can then be determined. A sound source attached to the ultrasound scanner can be used to locate the sensors with reference to the frame of the ultrasound scanner. The three dimensional location of each sensor with respect to the Ultrasound scanner can thus be determined, and used to define the ellipsoids described in the previous paragraph.

As it stands, one cannot simply transmit the m-sequence direct as shown in FIGS. 2A, 2B, 2C and 2D. Image-based Ultrasound Spectrography (IDUS), Acoustic Radiation Force Imaging (ARFI), and similar imaging modalities relay on the mechanism of radiation force to stimulate a target using a beam of ultrasound energy. The target then emits lower frequency sound with frequencies on the order of 0-40 kHz. The frequency content and waveform of this lower frequency is determined by the modulation envelope of the transmitted ultrasound signal. The process of combining a (low frequency) audio signal with a (high frequency) carrier is known as "modulation".

Figure 5:
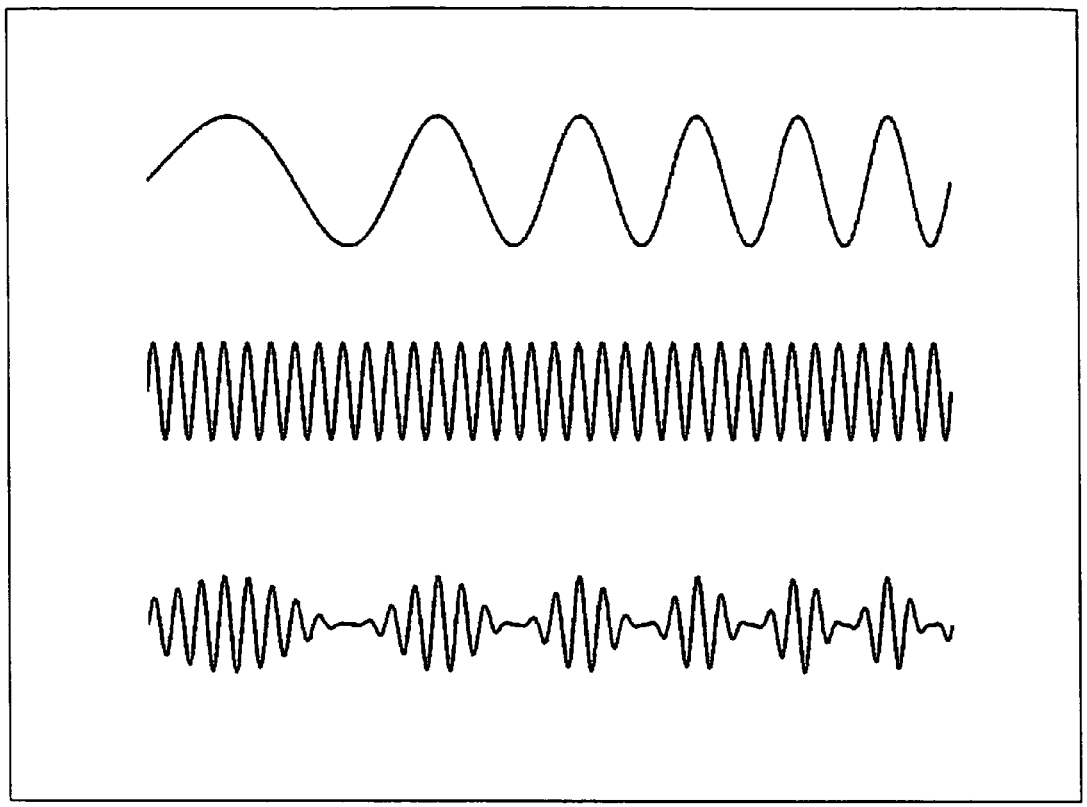
FIG. 5 shows the process of generating an amplitude modulated signal suitable for transmission by a carrier. The top waveform is the low frequency envelope signal (a chirp waveform in this example), the middle waveform is the higher frequency carrier signal, and the bottom waveform is the modulated carrier signal created by multiplying the upper two signals.
Figure 6:
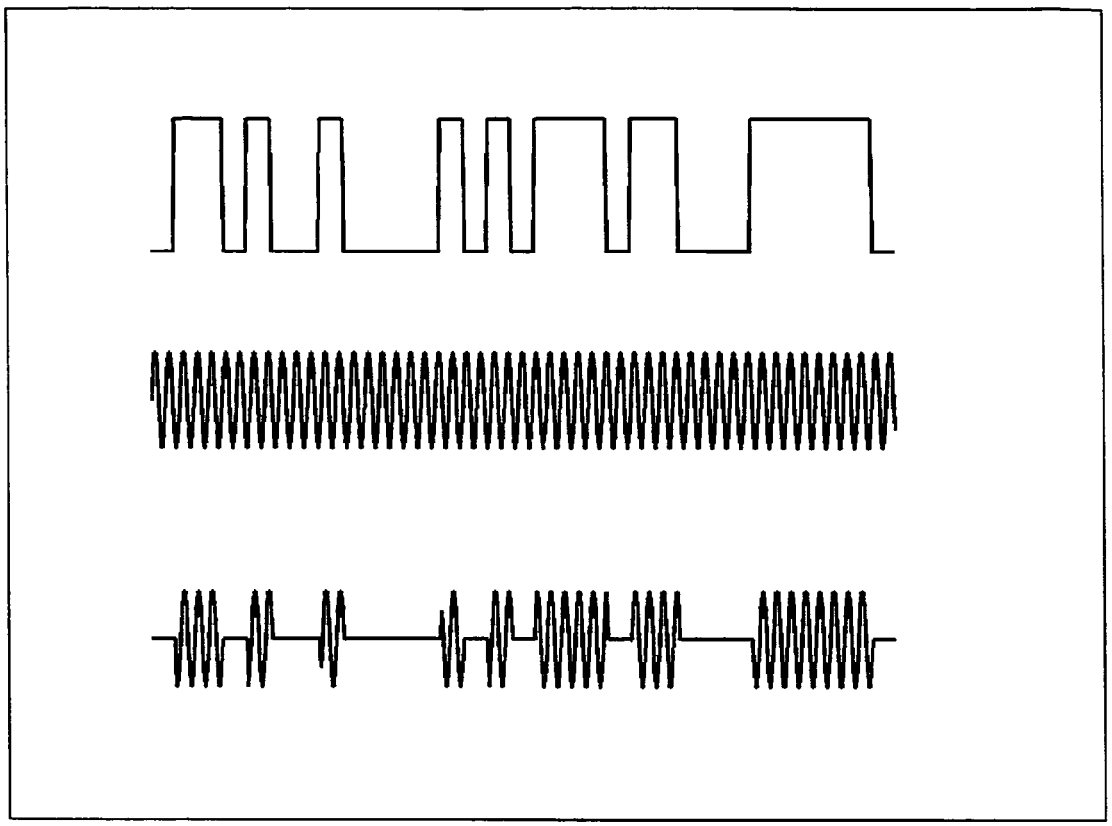
FIG. 6 shows the process of generating an amplitude modulated signal suitable for transmission by a carrier. The top waveform is the low frequency envelope signal, (a square waveform in this example), the middle waveform is the higher frequency carrier signal, and the bottom waveform is the modulated carrier signal created by multiplying the upper two signals. The square wave envelope could be based upon a pseudorandom or other digital sequence as described in the text.

FIG. 5 shows the process of generating an amplitude modulated signal suitable for transmission by a carrier. The carrier wave is multiplied by a lower frequency chirp waveform (the top waveform). The chirp is now contained in the amplitude (i.e., the envelope) of the modulated signal (shown in the bottom waveform). FIG. 6 shows the carrier wave multiplied by an m-sequence (the top waveform which assumes values of 0 and 1). The m-sequence is now contained in the amplitude (i.e., the envelope) of the modulated signal (shown in the bottom waveform). It is well known that this multiplication process used in these cases "shifts the spectrum" of the signal from the lower frequency range to the carrier frequency range. The process of demodulation is used to recover the modulation waveform. A simple amplitude modulation AM detector is a demodulator which would be familiar to a student of high school physics and comprises a diode (to remove the negative values of the signal) followed by a smoothing capacitor (to filter out the carrier). In this application, however, demodulation naturally occurs as a result of the physical properties of a microcalcification embedded in a viscoelastic medium. Radiation pressure is exerted on the target effectively depends on the square of the amplitude of the ultrasound transmitted signal. Note, the squared signal is a positive quantity. The viscoelastic material in contact with the target exerts a damping force (which acts to smooth the signal). The result is that the target will re-radiate the m-sequence embedded in the amplitude modulated signal that is incident upon it at the baseband frequencies of the modulation envelope.

Figure 7:
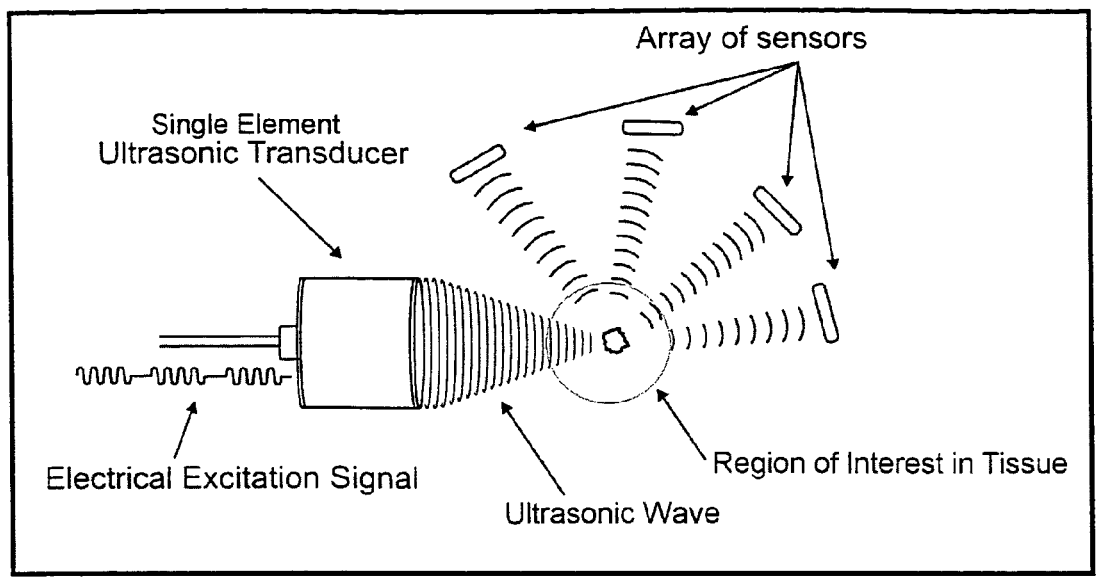
FIG. 7 is a diagram showing a single element ultrasonic transducer applying a modulated radiation force, or a modulated ultrasound signal, or a modulated beam of ultrasound wave energy to a target in a medium such as biological tissue and the reception of the resulting demodulated signals by an array of acoustic sensors.
Figure 8:
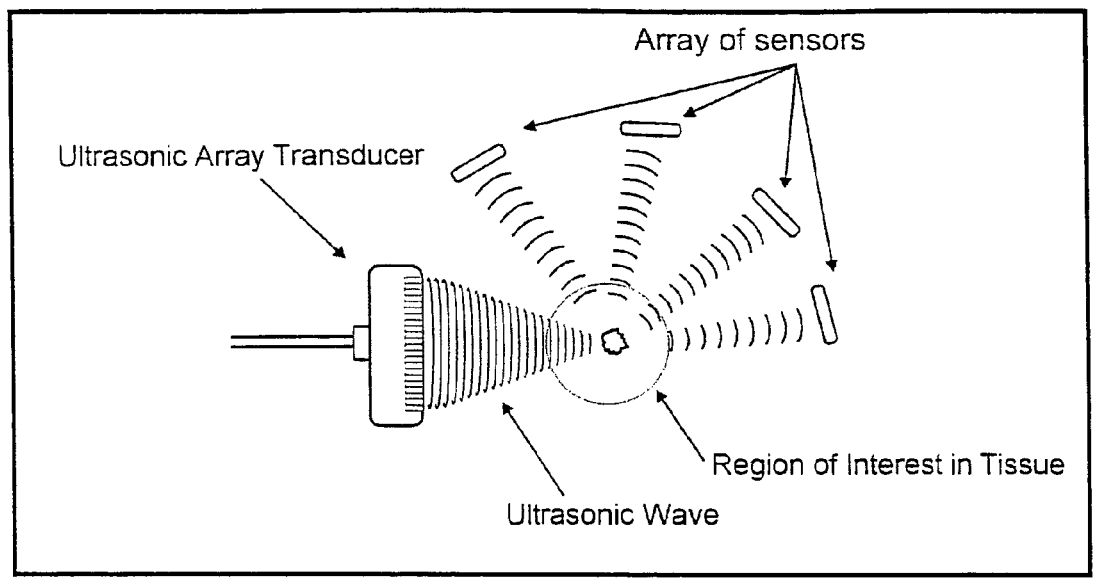
FIG. 8 is a diagram showing an ultrasonic array transducer applying a modulated radiation force, or a modulated ultrasound signal, or a modulated beam of ultrasound wave energy to a target in a medium such as biological tissue and the reception of the resulting demodulated signals by an array of acoustic sensors.

For example (see FIG. 7), an ultrasonic transducer operating in the range of 1-17 MHz emits an ultrasonic wave into biological tissue such as the tissues in a human breast. The m-sequence typically comprises 127 samples in the range of 1 to 200 kHz. Up sampling to a high sampling rate used for the carrier result in a $\sin(x)/x$ or sinc function squared spectral pattern that would be familiar to those skilled in the art. If a sample rate of 200 kHz is used, the spectrum is effectively flat over a 0-40 kHz range of interest.

The ultrasonic wave has a modulation envelope which creates a varying radiation force in the tissue medium. The radiation force will vary in proportion to the square of the amplitude of the modulation envelope and lower frequency signals (also known as demodulated signals) with waveforms, which follow the shape of the square of the modulation envelope, will thereby be generated. These lower frequency signals are then received by one or a multiplicity of sensors positioned at points surrounding the region of interest. The modulated ultrasonic wave may be created by exciting the transducer with an electrical excitation signal of the same form, i.e. a modulation envelope of the desired shape applied to a carrier frequency signal in the MHz range. The modulation envelope is selected so that the demodulated signals will have waveforms which follow a known pattern such as an m-sequence or chirp and are in the frequency range of 0 Hz to 40 kHz. Correlation techniques may then be applied to the received signals in order to accurately determine the amount of time which has passed between the transmission of the original ultrasound signal and the reception of the demodulated signals by a sensor, i.e. the time-of-flight of the sound waves. The time-of-flight values may in turn be used to ascertain the location of the source of the demodulated signals. Alternatively, correlation techniques may be used to determine the amount of demodulated signal being generated at a particular location and this information in turn used to characterize the tissue at that location and detect the presence of microcalcifications or other pathologies in the tissue.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A method of detecting a target in a medium, comprising:
    a. generating and transmitting an ultrasound signal having a modulation envelope and causing the ultrasound signal to impact the target;
    b. applying a coded modulation envelope having a specific auto-correlation function and a given band of frequencies to the transmitted ultrasound signal with the objective of improving the detection of signals generated by demodulation which occurs at the target;
    c. demodulating the ultrasound signal having a modulation envelope through the interaction of the ultrasound signal having a modulation envelope and the target and receiving the demodulated signal by at least one sensor;
    d. transmitting the ultrasound signal at an ultrasonic frequency and receiving the demodulation signal or signals at the frequency or frequencies of the applied modulation envelope;
    e. determining that a detected target is present in the medium by analyzing the received demodulated signal using at least one signal processing technique, the reception of signals are at frequencies which are not harmonically related to the transmitted ultrasound frequency and which are less than the transmitted ultrasound frequency; and
    f. demodulation at the target occurs prior to reception of the demodulated signal or signals as a result of the interaction of the modulated ultrasound signal and the target.

2. The method in accordance with claim 1 further comprising: determining a location of a detected target in at least one dimension in the medium by computing a time-of-flight of the demodulated signal to the least one sensor having a known location and determining the shortest time of flight to determine a direct path from the detected target to the at least one sensor, the direct path corresponding to the distance between the detected target and the at least one sensor.

3. The method in accordance with claim 1, further comprising: determining a location of a detected target in three dimensions in the medium by computing each time of flight of the demodulated signal to each of a multiplicity of at least three sensors having known locations and determining the shortest time of flight from at least three sensors to the detected target to determine each direct path from the detected target to each of the at least three sensors, each direct path corresponding to the distance between a respective of one of the three sensors and the detected target in the medium.

4. The method in accordance with claim 1, further comprising: the modulation envelope of the generated ultrasound signal is designed to supply stimulation energy to the target over a broad range of frequencies.

5. The method in accordance with claim 1, further comprising: the modulation envelope of the generated ultrasound signal based on a sequence whose cyclic auto-correlation function possesses a single finite maximum value and determining that a detected target is present in the medium by comparing the modulation envelope with the received demodulated signal using at least one correlation technique.

6. The method in accordance with claim 1, further comprising: the modulation envelope of the generated ultrasound signal is a chirp.

7. The method in accordance with claim 1, further comprising: the modulation envelope of the generated ultrasound signal is based on a pseudorandom sequence.

8. The method in accordance with claim 1, further comprising: the modulation envelope of the generated ultrasound signal is based on a maximum length sequence.

9. The method in accordance with claim 1, further comprising: the modulation envelope of the generated ultrasound signal is a Gold sequence.

10. The method in accordance with claim 1, further comprising: the auto-correlation function of the modulation envelope of the generated ultrasound signal possesses a single finite maximum value.

11. The method in accordance with claim 1, further comprising: the interference from multipath or clutter signals is reduced by using at least one signal processing technique selected from the group consisting of auto-correlation functions and cross-correlation functions.

12. The method in accordance with claim 1, further comprising: the medium is a human breast.

13. The method in accordance with claim 12, further comprising: the target is selected from the group consisting of a microcalcification in the human breast, a calcification in the human breast, a cluster of microcalcifications in the human breast and a cluster of calcifications in the human breast.

14. The method in accordance with claim 1, further comprising: using the method in conjunction with image-based dynamic ultrasound spectrography (IDUS).

15. The method in accordance with claim 1, further comprising: the target is a region of tissue with different density from the surrounding tissue.

16. The method in accordance with claim 1, further comprising: the generated ultrasound signal is obtained from an ultrasonic transducer selected from the group consisting of a single element transducer and an array transducer.

17. The method in accordance with claim 1, further comprising: the at least one sensor selected from the group consisting of: acoustic sensors, a microphone, microphones, a hydrophone, hydrophones, an accelerometer, accelerometers, a strain gauge, strain gauges, a surface microphone, surface microphones, a surface hydrophone and surface hydrophones.

18. The method in accordance with claim 2, further comprising: the medium is a human breast.

19. The method in accordance with claim 18, further comprising: the target is selected from the group consisting of a microcalcification in the human breast, a calcification in the human breast, a cluster of microcalcifications in the human breast and a cluster of calcifications in the human breast.

20. The method in accordance with claim 2, further comprising: using the method in conjunction with image-based dynamic ultrasound spectrography (IDUS).

21. The method in accordance with claim 2, further comprising: the at least one sensor selected from the group consisting of: acoustic sensors, a microphone, microphones, a hydrophone, hydrophones, an accelerometer, accelerometers, a strain gauge, strain gauges, a surface microphone, surface microphones, a surface hydrophone and surface hydrophones.

22. The method in accordance with claim 3, further comprising: the medium is a human breast.

23. The method in accordance with claim 20, further comprising: the target is selected from the group consisting of a microcalcification in the human breast, a calcification in the human breast, a cluster of microcalcifications in the human breast and a cluster of calcifications in the human breast.

24. The method in accordance with claim 3, further comprising: using the method in conjunction with image-based dynamic ultrasound spectrography (IDUS).

25. The method in accordance with claim 3, further comprising: the sensors selected from the group consisting of: acoustic sensors, a microphone, microphones, a hydrophone, hydrophones, an accelerometer, accelerometers, a strain gauge, strain gauges, a surface microphone, surface microphones, a surface hydrophone and surface hydrophones.

26. The method in accordance with claim 1, further comprising the at least one signal processing technique is selected from the group consisting of auto-correlation functions and cross-correlation functions.

27. A method of detecting a target in three dimensions in a human body, comprising:
   a. positioning an excitation transducer at a known location relative to the breast;
   b. positioning at least three acoustic sensors at known locations relative to the target, known locations relative to each other acoustic sensor, and known locations relative to the excitation transducer, each of the at least three acoustic sensors capable of acting as sound sources which permit the use of a flexible array matrix which flexible array matrix facilitates adaptability to different physical situations and facilitates acoustic coupling with the breast;
   c. generating an ultrasound signal having a modulation envelope from the excitation transducer and causing the ultrasound signal to impact the target;
   d. demodulating the ultrasound signal having a modulation envelope through the interaction of the ultrasound signal having a modulation envelope and the target, receiving the demodulated signal by the at least three acoustic sensors to detect that the target cluster is present in the human body;
   e. once it has been determined that the target cluster of microcalcifications is in the human body, determining a location of the detected target in three dimensions in the human body by computing each time-of-flight of the demodulated signal to each of the multiplicity of at least three sensors having known locations and determining the shortest time-of-flight from each of the at least three acoustic sensors to the detected target to determine each direct path from the detected target to each of the three acoustic sensors, each direct path corresponding to the distance between a respective one of the at least three sensors and the detected target in the human body;
   f. the modulation envelope of the generated ultrasound signal is selected from the group consisting of a chirp, based on a pseudo-random sequence, based on a maximum length sequence, based on a gold sequence, and is intended to improve reception of the reflected, re-radiated and demodulated signal in the presence of multi-path or clutter signals;
   g. for the time-of-flight measurement, measuring the impulse response of the transmission path since a first peak of an impulse response occurs at a time equal to the delay time of the transmission channel;
   h. the impulse response of the transmission path and therefore, the transmission delay is computed by determining the cross-correlation function of an input m-sequence with the corresponding received signal of the output channel. the position of the leading impulse showing the delay along the direct path and is used to determine distance from the transducer to the sensor;
   i. the impulse response of the transmission path enabling determination of the total time of flight between the excitation transducer to the target and from the target to the multiplicity of receiving sensors, the first significant peak in the impulse response of the transmission path corresponding to the direct linear path;
   j. the delay determined by this system corresponds to the total distance from the ultrasound transducer to the target plus the distance from the target to a given receiving sensor where points of constant total distance lie on an ellipsoid with the excitation transducer and a receiving sensor located at two focal points of an ellipse, wherein there is a separate ellipsoid for each receiving sensor so locating the target is equivalent to finding the point of intersection between a set of ellipsoids, so that the location of the target is at the intersection of the ellipsoids and also with the focal axis of the transmitted signal;

k. the receiving sensors designed so that they also are operated as sound sources, each sensor used to generate an m-sequence or chirp which is detected by the other sensors and decoded in a similar manner to a demodulated ultrasound signal received from a target, the distance between each sensor the stimulating transducer, and each of the other sensors is then be determined; and l. a sound source attached to an ultrasound scanner is used to locate with reference to the frame of the ultrasound scanner so that the three-dimensional location of each sensor with respect to the ultrasound scanner is therefore determined and used to define the ellipsoids in section "j" above.

28. A method of detecting a target cluster of breast micro-calcifications in three dimensions in a human body, comprising:

a. positioning an excitation transducer at a known location relative to the breast;

b. positioning at least three acoustic sensors at known locations relative to the breast, known locations relative to each other acoustic sensor, and known locations relative to the excitation transducer, each of the acoustic sensors capable of acting as sound sources which permit the use of a flexible array matrix which flexible array matrix facilitates adaptability to different physical situations and facilitates acoustic coupling with the breast;

c. generating an ultrasound signal having a modulation envelope from the excitation transducer and causing the ultrasound signal to impact the target cluster of breast calcifications;

d. demodulating the ultrasound signal having a modulation envelope through the interaction of the ultrasound signal having a modulation envelope and the target cluster of micro-calcifications, receiving the demodulated signal by the at least three acoustic sensors for the demodulated signal to detect that the target cluster of micro-calcifications is present in the breast;

e. once it has been determined that the target cluster of micro-calcifications is in the breast, determining a location of the detected target of breast micro-calcifications in three dimensions in the breast by computing each time-of-flight of the demodulated signal to each of the multiplicity of at least three sensors having known locations and determining the shortest time-of-flight from each of the three acoustic sensors to the detected target cluster of micro-calcifications to determine each direct path from the detected target breast micro-calcifications to each of the at least three acoustic sensors, each direct path corresponding to the distance between a respective one of the at least three sensors and the detected target in the breast; and f. the modulation envelope of the generated ultrasound signal is selected from the group consisting of a chirp, based on a pseudo-random sequence, based on a maximum length sequence, based on a gold sequence, and is intended to improve reception of the reflected, re-radiated and demodulated signal in the presence of multi-path or clutter signals; and g. for the time-of-flight measurement, measuring the impulse response of the transmission path since a first peak of an impulse response occurs at a time equal to the delay time of the transmission channel, and accomplishing this result by applying an m-sequence as spreading code or chipping sequence to be input at the excitation transducer; and h. computing the impulse response of the transmission path and therefore, the transmission delay by determining the cross-correlation function of an input m-sequence with the corresponding received signal of the output channel, the position of the leading impulse showing the delay along the direct path and is used to determine the position of the target cluster of breast micro-calcifications; and i. the impulse response of the transmission path enabling determination of the total time of flight between the excitation transducer to the target and from the target to the multiplicity of receiving sensors, the first significant peak in the impulse response of the transmission path corresponding to the direct linear path; and j. wherein the delay determined by this system corresponds to the total distance from the ultrasound transducer to the target plus the distance from the target to a given receiving sensor where points of constant total distance lie on an ellipsoid with the excitation transducer and a receiving sensor located at two focal points of an ellipse, wherein there is a separate ellipsoid for each receiving sensor so locating the target is equivalent to finding the point of intersection between a set of ellipsoids, so that the location of the target is at the intersection of the ellipsoids and also with the focal axis of the transmitted signal; and k. wherein the receiving sensors are designed so that they also are operated as sound sources, each sensor used to generate an m-sequence or chirp signal which is detected by the other sensors and decoded in a similar manner to a demodulated ultrasound signal received from a target, the distance between each sensor the stimulating transducer, and each of the other sensors can then be determined.

29. The method of detecting a target of breast microcalcifications in three dimensions in a human body in accordance with claim 28, further comprising: a sound source attached to an ultrasound scanner can be used to locate with reference to the frame of the ultrasound scanner so that the three-dimensional location of each sensor with respect to the ultrasound scanner is therefore determined and used to define the ellipsoids in section a of claim 28.

30. A method of detecting a target cluster of breast calcifications in three dimensions in a human body, comprising:

a. positioning an excitation transducer at a known location relative to the breast;

b. positioning at least one acoustic sensor at known locations relative to the breast, known locations relative to each other acoustic sensor, and known locations relative to the excitation transducer, each of the acoustic sensors capable of acting as sound sources which permit the use of a flexible array matrix which flexible array matrix facilitates adaptability to different physical situations and facilitates acoustic coupling with the breast;

c. generating an ultrasound signal having a modulation envelope from the excitation transducer and causing the ultrasound signal to impact the target cluster of breast calcifications;

d. demodulating the ultrasound Signal having a modulation envelope through the interaction of the ultrasound signal having a modulation envelope and the target cluster of micro-calcifications, receiving the demodulated signal by the at least one acoustic sensor to detect that the target cluster of micro-calcifications is present in the breast;

e. once it has been determined that the target cluster of micro-calcifications is in the breast, determining a location of the detected target of breast micro-calcifications in at least one dimension in the breast by computing each time-of-flight of the demodulated signal to each of the at least one sensor having known locations and determining the shortest time-of-flight from each of the at least one acoustic sensors to the detected target cluster of micro-calcifications to determine each direct path from the detected target breast micro-calcifications to each of the at least one acoustic sensors, each direct path corresponding to the distance between a respective one of the three sensors and the detected target in the breast; and f. the modulation envelope of the generated ultrasound signal is selected from the group consisting of a chirp, based on a pseudo-random sequence, based on a maximum length sequence, based on a gold sequence, and is intended to improve reception of the reflected, re-radiated and demodulated signal in the presence of multipath or clutter signals;

g. for the time-of-flight measurement, measuring the impulse response of the transmission path since a first peak of an impulse response occurs at a time equal to the delay time of the transmission channel, and accomplishing this result by applying an m-sequence as spreading code or chipping sequence to be input at the excitation transducer;

h. the impulse response of the transmission path and therefore, the transmission delay is computed by determining the cross-correlation function of an input m-sequence with the corresponding received signal of a sensor channel, the position of the leading impulse showing the delay along the direct path and is used to determine the position of the target branch cluster of micro-calcifications; and i. the impulse response of the transmission path enabling determination of the total time of flight between the excitation transducer to the target and from the target to the multiplicity of receiving sensors, the first significant peak in the impulse response of the transmission path corresponding to the direct linear path; and j. wherein the delay determined by this system corresponds to the total distance from the ultrasound transducer to the target plus the distance from the target to a given receiving sensor where points of constant total distance lie on an ellipsoid with the excitation transducer and a receiving sensor located at two focal points of an ellipse, wherein there is a separate ellipsoid for each receiving sensor so locating the target is equivalent to finding the point of intersection between a set of ellipsoids, so that the location of the target is at the intersection of the ellipsoids and also with the focal axis of the transmitted signal.

31. The method of detecting a target cluster region in three dimensions in a human body in accordance with claim 30, further comprising: the receiving sensors designed so that they also are operated as sound sources, each sensor used to generate an m-sequence or chirp which is detected by the other sensors and decoded in a similar manner to a demodulated ultrasound signal received from a target, the distance between each sensor the stimulating transducer, and each of the other sensors can then be determined.

32. The method of detecting a target cluster region in three dimensions in a human body in accordance with claim 31, further comprising: a sound source attached to an ultrasound scanner is used to locate with reference to the frame of the ultrasound scanner so that the three-dimensional location of each sensor with respect to the ultrasound scanner is therefore determined and used to define the ellipsoids.

* * * * *